US012653592B2

(12) United States Patent
Mei et al.

(10) Patent No.: US 12,653,592 B2
(45) Date of Patent: Jun. 16, 2026

(54) MEMORY ALLOY EPIPHYSEAL TRACTION SPLAYED NAIL AND SUPPORTING TOOL

(71) Applicant: Haibo Mei, Hunan (CN)

(72) Inventors: Haibo Mei, Changsha (CN); Xiongke Hu, Changsha (CN); Qian Tan, Changsha (CN); An Yan, Changsha (CN); Han Xiao, Changsha (CN)

(73) Assignee: Haibo MEI, Changsha (CN)

( * ) Notice: Subject to any disclaimer, the term of this patent is extended or adjusted under 35 U.S.C. 154(b) by 56 days.

(21) Appl. No.: 18/736,404

(22) Filed: Jun. 6, 2024

(65) Prior Publication Data

US 2024/0407819 A1 Dec. 12, 2024

(30) Foreign Application Priority Data

Jun. 9, 2023 (CN) .......................... 202310682820.2

(51) Int. Cl.
| | |
|---|---|
| *A61B 17/88* | (2006.01) |
| *A61B 17/00* | (2006.01) |
| *A61B 17/66* | (2006.01) |
| *A61B 17/72* | (2006.01) |

(52) U.S. Cl.
CPC .......... *A61B 17/8858* (2013.01); *A61B 17/66* (2013.01); *A61B 17/7225* (2013.01); *A61B 2017/00867* (2013.01)

(58) Field of Classification Search
CPC .............. A61B 17/885; A61B 17/0642; A61B 17/0682; A61B 17/7225; A61B 17/8863; A61B 2017/00867
See application file for complete search history.

(56) References Cited

U.S. PATENT DOCUMENTS

| | | | | |
|---|---|---|---|---|
| 10,376,367 | B2* | 8/2019 | Fallin ................. | A61B 17/8004 |
| 2003/0139746 | A1* | 7/2003 | Groiso .............. | A61B 17/0642 |
| | | | | 606/75 |
| 2013/0206815 | A1* | 8/2013 | Fox ........................ | A61B 50/30 |
| | | | | 227/176.1 |
| 2017/0252036 | A1* | 9/2017 | Palmer ................. | A61B 17/866 |
| 2017/0281157 | A1* | 10/2017 | Hartdegen ......... | A61B 17/8019 |
| 2017/0296174 | A1* | 10/2017 | Wahl .................. | A61B 17/0682 |
| 2018/0271521 | A1* | 9/2018 | Wahl .................. | A61B 17/0682 |
| 2024/0206924 | A1* | 6/2024 | Hyman .............. | A61B 17/8855 |

* cited by examiner

*Primary Examiner* — Eduardo C Robert
*Assistant Examiner* — Holly Joanna Lane
(74) *Attorney, Agent, or Firm* — Bochner PLLC; Andrew D. Bochner

(57) ABSTRACT

A memory alloy epiphyseal traction splayed nail and a supporting tool. The memory alloy epiphyseal traction splayed nail includes two nail arms, and a nail body. The two nail arms are connected to both ends of the nail body to form a splayed shape, the two nail arms form two sides of the splayed shape and are in circular arc transition with the nail body, and the two nail arms and the nail body are gradually transitioning from a compressed state to a stable state through deformation, so as to gradually promote growth of an epiphyseal plate of a long bone on an implantation side. The compressed state is a state in which the two nail arms are configured for implantation, and the stable state is a state in which the two implanted nail arms gradually restore their shapes.

8 Claims, 4 Drawing Sheets

MEMORY ALLOY EPIPHYSEAL TRACTION SPLAYED NAIL AND SUPPORTING TOOL

CROSS-REFERENCE TO RELATED APPLICATION

This patent application claims the benefit and priority of Chinese Patent Application No. 2023106828202 filed with the China National Intellectual Property Administration on Jun. 9, 2023, the disclosure of which is incorporated by reference herein in its entirety as part of the present application.

TECHNICAL FIELD

The present disclosure relates to the technical field of guided growth of bones, in particular to a memory alloy epiphyseal traction splayed nail and a supporting tool.

BACKGROUND

The development of human skeleton is mainly divided into two processes, i.e., intramembranous ossification and endochondral ossification. The intramembranous ossification involves in the growth of craniofacial skeleton, while the endochondral ossification is crucial for the growth of axial and long bone skeleton. The growth of height is driven by the elongation of long bones caused by the formation of cartilage in epiphyseal plate (also known as growth plate). The growth plate is located between epiphysis and metaphysis, and consists of three zones (resting zone, proliferation zone, and hypertrophic zone). Each zone contains various chondrocytes at different stages of differentiation, and bone growth is jointly promoted through the proliferation and differentiation of chondrocytes, calcification in the hypertrophic zone, invasion and differentiation of osteoblasts.

Under physiological conditions, the growth plate drives bone growth through the complex network organization of human nutrition, cells, paracrine and endocrine factors until the closure of the growth plate. However, some other factors, such as combined abnormal hormone secretion, trauma, tumor and so on, will affect the normal driving of the growth plate, resulting in skeletal dysplasia, causing skeletal arched deformity, varus/valgus deformity, premature closure of the epiphyseal plate and other symptoms. When growth plate development diseases occur, conservative treatment is ineffective and surgery is often needed.

At present, osteotomy and epiphyseal block surgery are commonly used for skeletal deformity caused by abnormal driving of the growth plate. Osteotomy is traumatic and bleeding, and has many complications such as wound infection, nerve injury, and nonunion of osteotomy zone. Epiphyseal block surgery is to suppress the growth of the epiphyseal plate on one side by internal fixation combined with engineering mechanics, while keep the normal growth of the epiphyseal plate on an opposite side, thus achieving the correction of skeletal angulation deformity. However, by suppressing the growth of the epiphyseal plate on one side of the affected limb and forcing the growth of the long bone on both sides consistent, with the correction of metaphyseal deformity, the problem of shortening of the limb on this side may occur. Epiphyseal block surgery through epiphyseal screws is accompanied with the risk of bone bridge formation in epiphyseal plate and premature closure of epiphyseal plate.

SUMMARY

The technical problem to be solved by the present disclosure is to overcome the shortcomings in the prior art, and provide a memory alloy epiphyseal traction splayed nail and a supporting tool. The design feature of the nail is suitable for anatomical structure of metaphysis and epiphysis of a long bone. The memory alloy epiphyseal traction splayed nail is convenient and firm to install, closely fits the bone, and small in size when installed, and there are no problems such as difficulty in incision suture and exposure of internal fixation caused by skin dehiscence.

To achieve the objective above, the present disclosure provides the following technical solution:

A memory alloy epiphyseal traction splayed nail includes two nail arms configured for implantation in epiphysis and metaphysis, and a nail body placed outside metaphysis and epiphysis and spanning an epiphyseal plate. The two nail arms are connected to both ends of the nail body to form a splayed shape. The two nail arms form two sides of the splayed shape and are in circular arc transition with the nail body, so it is named as an epiphyseal splayed nail. The two nail arms and the nail body are capable of gradually transitioning from a compressed state to a stable state through deformation, so as to gradually promote growth of an epiphyseal plate of a long bone at an implantation side. The compressed state is a state in which the two nail arms are configured for implantation, and the stable state is a state in which the two implanted nail arms gradually restore their shapes. Inverted teeth for preventing withdrawal are uniformly arranged on the two nail arms.

As a further improvement of the technical solution above:

An included angle between each of the two nail arms and the nail body in the stable state is in a range of 105°~120°.

A tip part connected to the inverted teeth is arranged at a tail end of each of the two nail arms.

The inverted teeth include multiple tooth tips, the multiple tooth tips are uniformly arranged in an implantation direction, and each of the tooth tips is formed in a tooth shape opposite to the implantation direction.

Each of the tooth tips is formed by connecting a first inclined plane with a second inclined plane, and the first inclined plane is close to the tip part, and the second inclined plane is away from the tip part.

A width of the first inclined plane in the implantation direction is greater than a width of the second inclined plane in the implantation direction.

The inverted teeth are located at sides, on which the two nail arms face each other, of the two nail arms.

A supporting tool includes a drill. A grip handle is arranged on one end of the drill, a drill bit is arranged on another end of the drill for positioning an implantation point on each of the metaphysis and the epiphysis.

The supporting tool includes a clamp with two operating rods. A supporting frame capable of adjusting distance between pressing ends of the two operating rods is arranged between the pressing ends of the two operating rods, and clamping ends of the two operating rods are configured for clamping the two nail arms, thus making the included angle between each of the two nail arms and the nail body being acute.

Compared with the prior art, the present disclosure achieves beneficial effects as follows:

According to the present disclosure, the two nail arms can be conveniently inserted through pre-drilled implantation holes in the metaphysis and the epiphysis, making the installation operation convenient. The inverted teeth can prevent the inserted nail arms from displacing or even withdrawing, and the firm connection is achieved through the nail body. The overall volume after installation is small, without affecting the suturing and healing of the incision. The traction splayed nail, when in a stable state, is in a splayed shape as a whole. Before implantation, the traction splayed nail is pre-bent into a compressed state and compressed into a proper angle. After implantation, the splayed nail slowly opens and restores to the stable state, which drives the traction of a growth plate zone on the implantation side and promotes the gradual growth of the long bone. Through the guided growth technique of the traction splayed nail, the epiphyseal plate of the long bone grows gradually to improve skeletal deformity, so as to achieve the orthopedic purpose. The traction splayed nail is suitable for bone diseases caused by abnormal driving of the growth plate, such as leg length discrepancy, knee valgus, knee varus, ankle valgus, and genu varum.

100 metaphysis; 200 epiphysis; 1 nail arm; 2 nail body; 3 inverted tooth; 4 tip part; 5 drill; 51 grip handle; 52 drill bit; 6 clamp; 61 operating rod; 62 supporting frame.

DETAILED DESCRIPTION OF THE EMBODIMENTS

The present disclosure is further described below with reference to accompanying drawings and specific embodiments.

Figure 1:
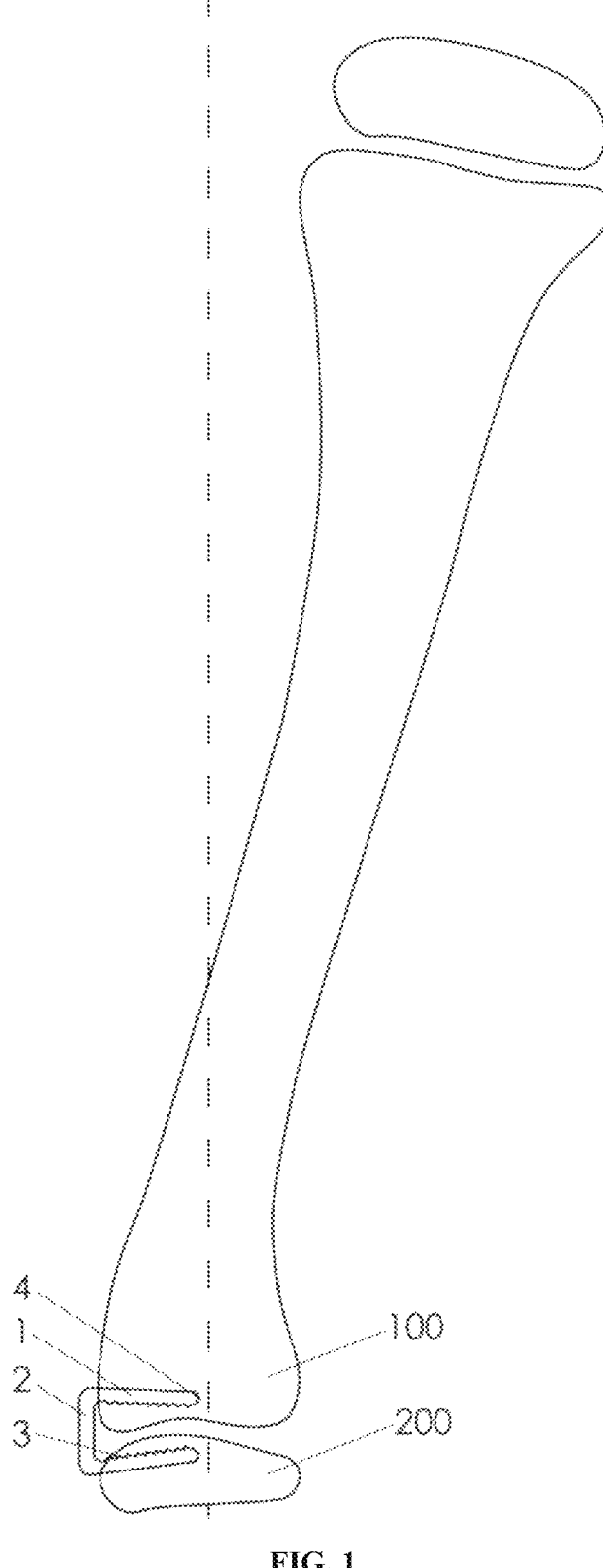
FIG. 1 is a structural schematic diagram of a memory alloy epiphyseal traction splayed nail in a compressed state after implantation.
Figure 2:
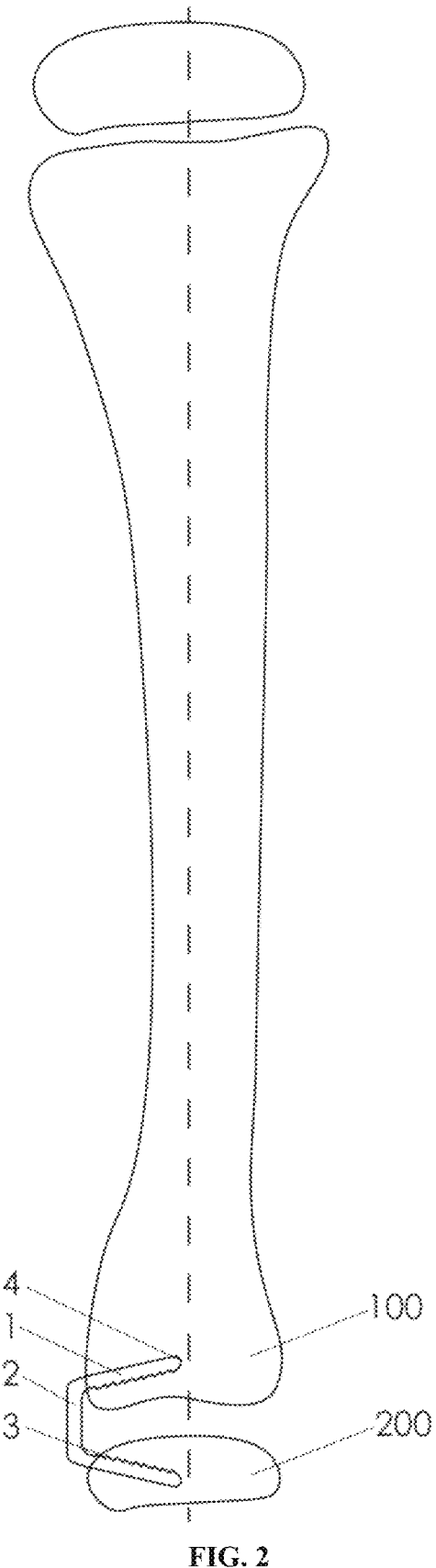
FIG. 2 is a structural schematic diagram of a memory alloy epiphyseal traction splayed nail in a stable state after implantation.
Figure 3:
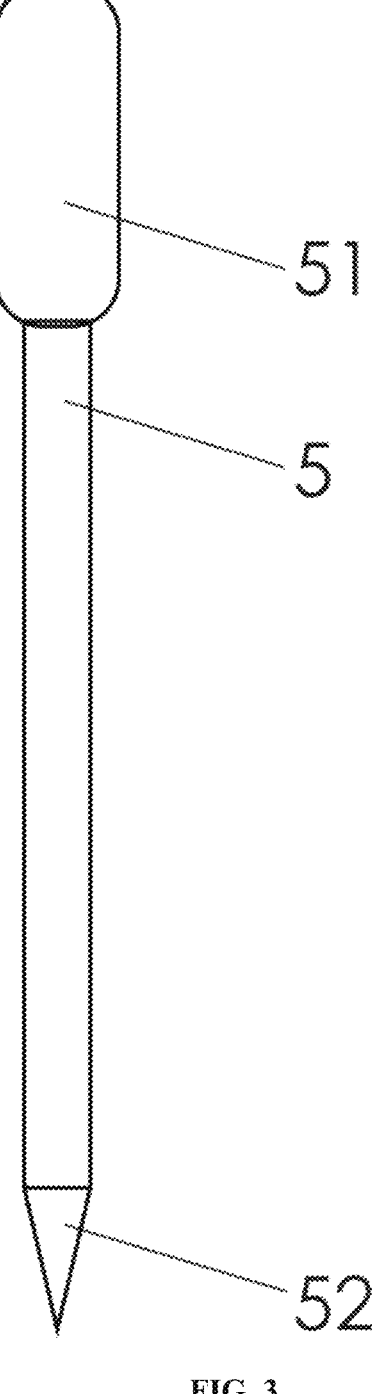
FIG. 3 is a structural schematic diagram of a drill.
Figure 4:
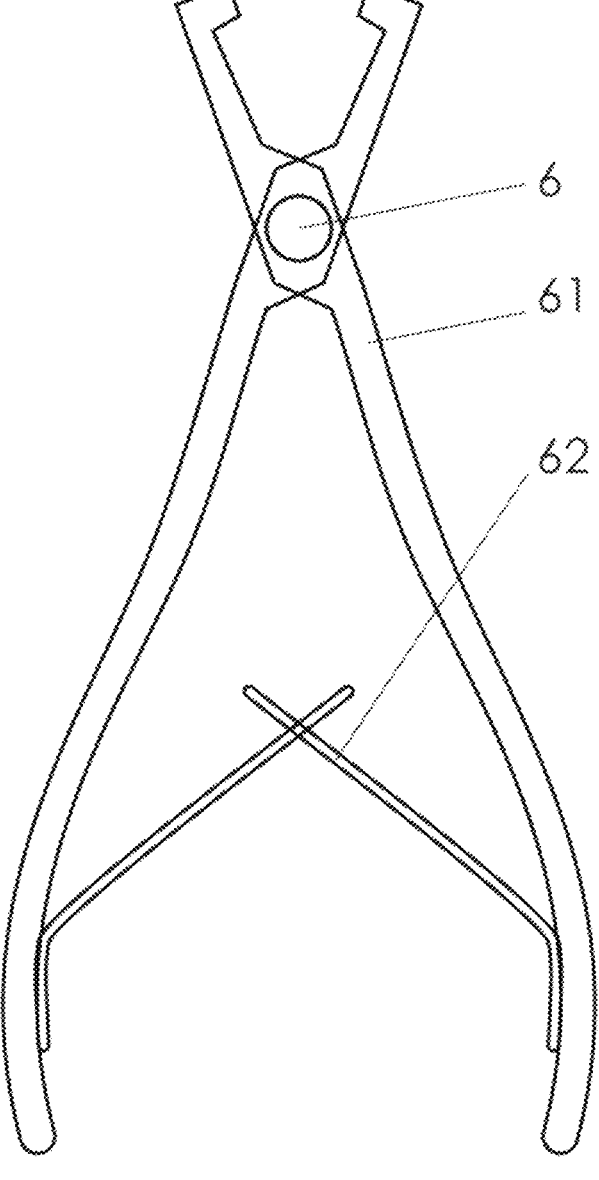
FIG. 4 is a structural schematic diagram of a clamp.

As shown in FIG. 1 to FIG. 4, a memory alloy epiphyseal traction splayed nail in this embodiment includes two nail arms 1 configured for implantation in metaphysis 100 and epiphysis 200, respectively, and a nail body 2 placed outside the metaphysis 100 and the epiphysis 200 and spanning an epiphyseal plate. The two nail arms 1 are connected to both ends of the nail body 1 to form a splayed shape. The two nail arms 1 form two sides of the splayed shape, and are in circular arc transition with the nail body 1. The two nail arms 1 and the nail body 2 are gradually transitioning from a compressed state to a stable state through deformation, so as to gradually promote growth of an epiphyseal plate of a long bone at an implantation side. The compressed state is a state in which the two nail arms 1 are used for implantation, and the stable state is a state in which the two implanted nail arms 1 gradually restore their shapes. Inverted teeth 3 for preventing withdrawal are uniformly arranged on the two nail arms 1. According to the present disclosure, the two nail arms 1 can be conveniently inserted through pre-drilled implantation holes in the metaphysis 100 and the epiphysis 200, making the installation operation convenient. The inverted teeth 3 can prevent the inserted nail arms 1 from displacing or even withdrawing, and the firm connection is achieved through the nail body 2. The overall volume after installation is small, without affecting the suturing and healing of the incision. The traction splayed nail, when in a stable state, is in a splayed shape as a whole. Before implantation, the traction splayed nail is pre-bent into a compressed state and compressed into a proper angle. After implantation, the splayed nail slowly opens and restores to the stable state, at this time, the two nail arms 1 are similar to a splayed shape, thus driving the traction of a growth plate zone on the implantation side and promoting the gradual growth of the long bone. Through the guided growth technique of the traction splayed nail, the epiphyseal plate of the long bone grows gradually to improve skeletal deformity, so as to achieve the orthopedic purpose. The traction splayed nail is suitable for bone diseases caused by abnormal driving of the growth plate, such as leg length discrepancy, knee valgus, knee varus, ankle valgus, and genu varum. Compared with epiphyseal block surgery, the traction splayed nail spans the growth plate for distraction and traction, more growth space is reserved for the limb. The inverted teeth 3 can reduce the risk of loosening and withdrawal of the nail arms 1.

In this embodiment, an included angle between each of the two nail arms 1 and the nail body 2 in the stable state is in a range of 105°~120°. The included angle range is a preferable and appropriate range, which can limit the stretching of a growth plate zone on the implantation side to an appropriate distance.

In this embodiment, a tip part 4 connected to the inverted teeth 3 is arranged at a tail end of each of the two nail arms 1. The nail arm 1 can be conveniently inserted into a hole drilled by the drill 5 in advance through the tip part 4, and the stable installation is guaranteed while the implantation is convenient.

In this embodiment, the inverted teeth 3 include multiple tooth tips, the multiple tooth tips are uniformly arranged in an implantation direction, and each of the tooth tips is formed in a tooth shape opposite to the implantation direction. The firmness of installation of the two nail arms 1 can be further improved through multiple tooth tips being formed in a tooth shape.

In this embodiment, each of the tooth tips is formed by connecting a first inclined plane with a second inclined plane, and the first inclined plane is close to the tip part 4, and the second inclined plane is away from the tip part 4. By providing the first inclined plane and the second inclined plane, the processing and manufacturing is facilitated, and the manufacturing cost is reduced.

In this embodiment, a width of the first inclined plane in the implantation direction is greater than a width of the second inclined plane in the implantation direction. The wider first inclined plane is beneficial to quickly penetrate into the implantation hole, and the narrower second inclined plane can avoid minor displacement.

In this embodiment, the inverted teeth 3 are located at sides, on which the two nail arms face each other, of the two nail arms 1. The design of the inverted teeth 3 can prevent the implanted screws from loosening or withdrawing.

In this embodiment, a supporting tool includes a drill 5. A grip handle 51 is arranged on one end of the drill 5, and a drill bit 52 is arranged on another end of the drill 5 for positioning an implantation point on each of the metaphysis 100 and the epiphysis 200. The drill 5 is convenient for the positioning of implantation points on the metaphysis 100 and the epiphysis 200, with convenient operation. During operation, when the traction splayed nail is compressed, an implantation point on each of the metaphysis 100 and the epiphysis 200 is selected according to the distance between the two nail arms 1, and the drill bit 52 is inserted into the implantation point and then pulled out when reaching an appropriate depth.

In this embodiment, the supporting tool includes a clamp 6 with two operating rods 61. A supporting frame 62 capable of adjusting distance between pressing ends of the two operating rods 61 is arranged between the pressing ends of the two operating rods 61, and clamping ends of the two operating rods 61 are configured for clamping the two nail arms 1, thus making the included angle between each of the two nail arms 1 and the nail body 2 being acute. The traction splayed nail can be conveniently compressed through the clamp 6, with convenient operation. The two nail arms 1 are implanted at the clamping ends, pressure is applied through the pressing ends, and then the force is transmitted to the clamping ends, making the two nail arms 1 compressed and deformed towards each other.

In this embodiment, the length of each of the two nail arms 1 can be set according to the difference in width between the metaphysis 100 and the epiphysis 200.

The above is only the preferred embodiment of the present disclosure, and the scope of protection of the present disclosure is not limited to the above embodiments. For those of ordinary skill in the art, various improvements and changes made without departing from the technical concept of the present disclosure shall be regarded as the scope of protection of the present disclosure.

What is claimed is:

1. A memory alloy epiphyseal traction splayed nail, comprising two nail arms (1) configured for implantation in metaphysis (100) and epiphysis (200), and a nail body (2) placed outside metaphysis (100) and epiphysis (200) and spanning an epiphyseal plate, wherein the two nail arms (1) are connected to both ends of the nail body (2) to form a splayed shape; the two nail arms (1) form two sides of the splayed shape and are in circular arc transition with the nail body (2), and the two nail arms (1) and the nail body (2) are capable of gradually transitioning from a compressed state to a stable state through deformation, so as to gradually promote growth of an epiphyseal plate of a long bone on an implantation side; the compressed state is a state in which the two nail arms (1) are configured for implantation, and the stable state is a state in which two implanted nail arms (1) gradually restore their shapes; and inverted teeth (3) for preventing withdrawal are uniformly arranged on the two nail arms (1);

wherein an included angle between each of the two nail arms (1) and the nail body (2) in the stable state is in a range of 105°~120°;

wherein a tip part (4) connected to the inverted teeth (3) is arranged at a tail end of each of the two nail arms (1);

wherein the inverted teeth (3) comprise a plurality of tooth tips, the plurality of tooth tips are uniformly arranged in an implantation direction, and each of the tooth tips is formed in a tooth shape opposite to the implantation direction; and wherein a width of the first inclined plane in the implantation direction is greater than a width of the second inclined plane in the implantation direction.

2. The memory alloy epiphyseal traction splayed nail according to claim 1, wherein each of the tooth tips is formed by connecting a first inclined plane with a second inclined plane, and the first inclined plane is close to the tip part (4), and the second inclined plane is away from the tip part (4).

3. The memory alloy periosteal traction plate according to claim 1, wherein the inverted teeth (3) are located on sides, on which the two nail arms face each other, of the two nail arms (1).

4. A supporting tool of the memory alloy periosteal traction plate according to claim 1, further comprising a drill (5), wherein a grip handle (51) is arranged on one end of the drill (5), a drill bit (52) is arranged on another end of the drill (5) for positioning an implantation point on each of the metaphysis (100) and the epiphysis (200).

5. A supporting tool of the memory alloy periosteal traction plate according to claim 2, further comprising a drill (5), wherein a grip handle (51) is arranged on one end of the drill (5), a drill bit (52) is arranged on another end of the drill (5) for positioning an implantation point on each of the metaphysis (100) and the epiphysis (200).

6. A supporting tool of the memory alloy periosteal traction plate according to claim 3, further comprising a drill (5), wherein a grip handle (51) is arranged on one end of the drill (5), a drill bit (52) is arranged on another end of the drill (5) for positioning an implantation point on each of the metaphysis (100) and the epiphysis (200).

7. A supporting tool of the memory alloy periosteal traction plate according to claim 1, comprising a clamp (6) with two operating rods (61), wherein a supporting frame (62) capable of adjusting distance between pressing ends of the two operating rods (61) is arranged between the pressing ends of the two operating rods (61), and clamping ends of the two operating rods (61) are configured for clamping the two nail arms (1), thus making the included angle between each of the two nail arms (1) and the nail body (2) being acute.

8. A supporting tool of the memory alloy periosteal traction plate according to claim 2, comprising a clamp (6) with two operating rods (61), wherein a supporting frame (62) capable of adjusting distance between pressing ends of the two operating rods (61) is arranged between the pressing ends of the two operating rods (61), and clamping ends of the two operating rods (61) are configured for clamping the two nail arms (1), thus making the included angle between each of the two nail arms (1) and the nail body (2) being acute.

* * * * *